United States Patent [19]

Zeng et al.

[11] Patent Number: 5,170,439
[45] Date of Patent: Dec. 8, 1992

[54] CONE BEAM RECONSTRUCTION USING COMBINED CIRCLE AND LINE ORBITS

[75] Inventors: Gengsheng L. Zeng; Grant T. Gullberg, both of Salt Lake City, Utah; Hugh T. Morgan, Highland Heights, Ohio

[73] Assignee: Picker International, Inc., Highland Hts., Ohio

[21] Appl. No.: 713,719

[22] Filed: Jun. 11, 1991

[51] Int. Cl.[5] .......................................... G06K 9/00
[52] U.S. Cl. .................................. 382/6; 364/413.16; 364/413.20; 378/901
[58] Field of Search ................ 382/6, 54; 364/413.13, 364/413.15, 413.16, 413.19, 413.2; 358/111; 378/901

[56] References Cited

U.S. PATENT DOCUMENTS

| | | | |
|---|---|---|---|
| 4,205,375 | 5/1980 | Inouye et al. | 364/413.2 |
| 4,446,521 | 5/1984 | Inouye | 378/901 |
| 4,606,004 | 8/1986 | Crawford et al. | 382/6 |
| 4,616,318 | 10/1986 | Crawford | 364/413.2 |
| 4,851,984 | 7/1989 | Doi et al. | 382/6 |
| 4,894,775 | 1/1990 | Kritchman et al. | 364/413.16 |
| 4,979,111 | 12/1990 | Nishimura | 364/413.16 |

Primary Examiner—Jose Couso
Attorney, Agent, or Firm—Fay, Sharpe, Beall, Fagan, Minnich & McKee

[57] ABSTRACT

Radiation passing through a cone-beam collimator is received by a radiation detector, such as a gamma camera head, as the gamma camera head is moved in a circular orbit and in a line orbit. Data collected during the circular orbit is stored (42c), transformed (50c) into the frequency domain and redundant data removed (52c, 52c), and transformed (56c) back to the spatial domain. The data collected during the line orbit is stored (42l). The line orbit data is transformed to the frequency domain and repeatedly filtered with a family of filter functions (52l, 54) to remove redundant data. Each filter function corresponds to a different row through the examination region. The filtered frequency domain slice data sets ($62_1, 62_2, \ldots, 62_n$) are transformed (56l) back to the spatial domain and transferred to a central portion of a spatial domain memory (58l). Empty memory cells of the memory (58l) are filled with zeros. The spatial domain data from memories (58c, 58l) are filtered (72c, 72l), backprojected (74c, 74l), and summed (76) into a three-dimensional image representation that is stored in an image memory (78).

14 Claims, 6 Drawing Sheets

CONE BEAM RECONSTRUCTION USING COMBINED CIRCLE AND LINE ORBITS

This invention was made with government support under Grant No. HL 39792-03 awarded by the National Institutes of Health. The government has certain rights in the invention.

BACKGROUND OF THE INVENTION

The present invention relates to the art of diagnostic imaging. It finds particular application in conjunction with single photon emission computed tomography (SPECT) scanners with cone-beam collimation for medical diagnostic imaging and will be described with particular reference thereto. It is to be appreciated, however, that the invention will have other applications in which cone-beam type data is reconstructed into an image representation for medical, quality assurance, and other examinations. Although described in conjunction with the emission radiation sources which emit radiation from the subject, it will be appreciated that the present invention is also applicable to reconstructing image representation from transmission radiation sources which transmit radiation through a subject.

Cone-beam collimators are commonly used with single photon emission computed tomography and other gamma camera devices. The cone-beam collimator diverges outward from a subject face toward the scintillation crystal or detector head. This enables a large fraction of the detector head crystal face to be utilized when imaging relatively small regions of the patient, e.g. the heart. This effective magnification produces a combination of resolution and sensitivity gains over images formed using parallel or fan beam collimators.

Most commonly, cone-beam projection data is converted into image representations using a technique developed by Feldkamp, Davis, and Kress which is described in "Practical Cone-Beam Algorithm", J. Opt. Soc. Am. Vol. I, pp. 612-619 (1984). The Feldkamp technique uses an algorithm which was derived using approximations of a fan beam formula. A fan beam commonly lies in a single plane, but diverge in that plane. When multiple fan beams are used concurrently, the planes are substantially parallel. In this manner, the radiation paths diverge along one axis and are parallel in the other axis of the plane of reception.

Feldkamp, et al. use a convolution and backprojection method which assumes that the focal point orbit is a circle. However, if the focal point of the collimator follows a single, planar orbit, the obtained data is not sufficient for an exact three-dimensional reconstruction. The insufficiency in the amount of collected data causes distortions and artifacts in the resultant image.

In order to generate a complete or sufficient set of data, every plane which passes through the imaging field of view must also cut through the orbit of the focal point at least once. See Tuy "An Inversion Formula for Cone-Beam Reconstruction", SIAM J. Appl. Math. Vol. 43, pp. 546-552 (1983). The single planar orbit of Feldkamp does not satisfy this condition.

Another approach is to convert the cone-beam projections to Radon transforms and use the Radon inversion formula to reconstruct the image. This technique involves rebinning or sorting of the cone-beam data into another format. See Grangeat "Analysis d'un Systeme D'Imagerie 3D par Reconstruction a Partir De X en Geometrie Conique" Ph.D. Thesis l'Ecole Nationale Superieure Des Telecommunications (1987).

Others have proposed mathematical improvements to the reconstruction algorithms. For example, the cone-beam data sets can be inverted if one assumes that for any line that contains a vertex point and a reconstruction point, there is an integer M (which remains constant for the line) such that almost every plane that contains this line intersects the geometry exactly M times. See Smith "Cone-Beam Tomography: Recent Advances and a Tutorial Review", Optical Engineering, Vol. 29 (5), pp. 524-534 (1990). However, this integer requirement condition is too restrictive for practical application. The only known source point geometry which meets this condition is a straight line.

SUMMARY OF THE INVENTION

In accordance with the present invention, a new and improved cone-beam reconstruction technique is provided. To collect one set of data, a focal point of a cone-beam detection system is moved along (1) a circular orbit and (2) a line orbit. The data produced along the circle and line orbit taken together is more than a sufficient or complete set of data. The data from the circular orbit is transformed into and filtered in the frequency domain to remove extra and redundant data. The line orbit data is transformed into the frequency domain and divided into a plurality of rows. Each of the rows is operated upon with its own filter function or kernel to remove the redundant and unnecessary data. The remaining portions of the circle orbit data and the line orbit data are transformed to the spatial domain and reconstructed into a three-dimensional image representation.

In accordance with a more limited aspect of the present invention, the line orbit data filter function is a spatially varying two-dimensional filter which is derived by transforming a corresponding filter kernel for each row in the spatial domain into the frequency domain.

In accordance with another more limited aspect of the present invention, the filtered line orbit rows of data are reassembled. The assembled data is weighted and filtered row by row before reconstruction.

In accordance with another more limited aspect of the present invention, the circular orbit data is also weighted and filtered line by line. The weighted and filtered line and circular data is backprojected to create a three-dimensional image representation.

One advantage of the present invention is that it generates accurate three-dimensional images from cone-beam data.

Another advantage of the present invention is relative freedom from artifacts and distortion in the resultant image.

Yet another advantage of the present invention resides in its computational efficiency.

Still further advantages of the present invention will become apparent to those of ordinary skill in the art upon reading and understanding the following detailed description.

BRIEF DESCRIPTION OF THE DRAWINGS

The invention may take form in various components and arrangements of components. The drawings are only for purposes of illustrating the preferred embodiment and are not to be construed as limiting the invention.

DETAILED DESCRIPTION OF THE PREFERRED EMBODIMENTS

Figure 1A:
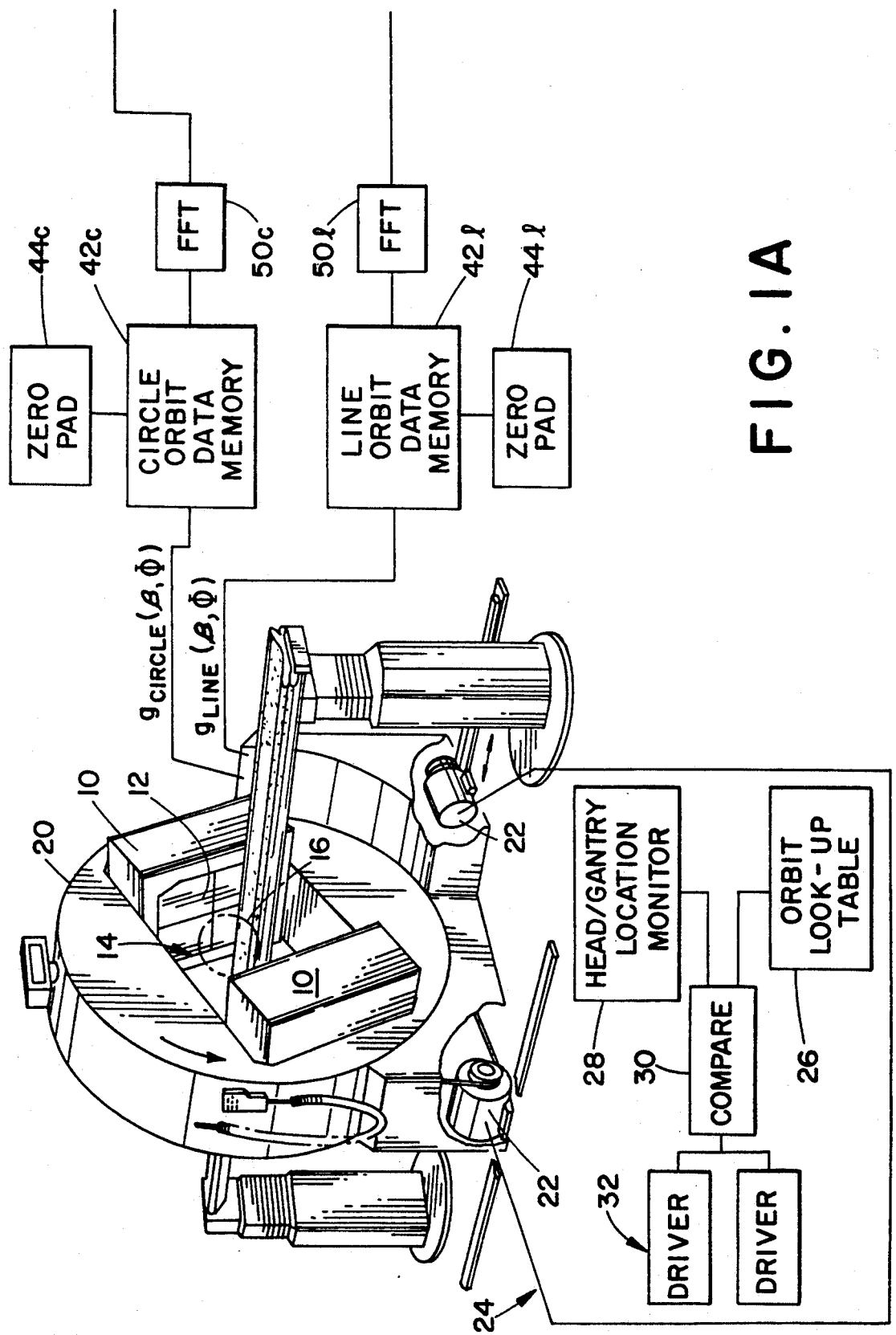
FIGS. 1A and 1B taken together are a diagrammatic illustration of a SPECT camera system in accordance with the present invention.

With reference to FIG. 1A, a cone-beam radiation detection means, such as one or more gamma camera heads 10, each with a cone-beam collimator 12, is mounted to move rotationally around and linearly along an examination region 14. The cone-beam collimator 12 has a plurality of paths defined by bores in a solid lead sheet or by lead vanes which focus at a focal point 16. The cone-beam collimator is oriented such that the focal point 16 is disposed across the examination region from a subject 18. Radiation emanating from the subject or passing through the subject follows diverging paths through the collimator to the gamma camera head or other detector. In this manner, a relatively small region of the subject is projected onto a relatively large region of a crystal face of the detector head 10, i.e. an effective magnification.

The detector heads are mounted on a gantry means or portion 20. The gantry means includes a plurality of motor drives 22 which can be operated individually or in combination in order to move the detector heads along selectable orbits. The heads are rotated along a circular orbit and the gantry is translated to move the heads along a line orbit. An orbit controller 24 generates motor control signals for each of the motors to cause the heads to move along the selected orbit. More specific to the illustrated embodiment, the orbit controller includes a look-up table 26 which is preprogrammed to the position and orientation in which the detector heads and gantry should be at each incremental stage of the orbit. The look-up table is preprogrammed with the appropriate positions which the gantry should take in order to move in the line orbit and the appropriate positions that the head should take when it moves in a circular orbit. A current position sensing means 28 monitors the current position of the detector head(s), such as by monitoring the angular position around the subject, the radial position toward and away from the subject, and the longitudinal position along the subject. A comparing means 30 compares the look-up table values with the actual rotational and longitudinal positions of the detector heads and gantry. A series of motor drivers 32 supply motive power to the motors or linear drive means 22 until the monitored current position matches the desired position from the look-up table. Optionally, descriptions of other orbits may be loaded into the look-up table 24.

The gantry or an associated control console includes a data processing means for processing the output data from the detector head(s). More specifically, each detector head conventionally includes a scintillation crystal that is viewed by an array of photomultiplier tubes. Each time a radiation event occurs, the radiation passing through the collimator and striking the crystal causes a light flash or scintillation. The photomultiplier tubes nearest the scintillation respond with proportional output signals. Position and energy resolving circuitry connected to the photomultiplier tubes determine the energy and position, hence the ray or direction along which the radiation travelled from the radiation event within the subject through the collimator to the detector head. Due to the cone-beam collimator, there is a direct relationship between the x, y position on the scintillation crystal at which the radiation was received and the directional vector $\beta$ of the ray. See FIG. 3.

Output data $g_{circle}(\beta,\Phi)$ from the head during the circular orbit $\Phi$ is stored in a circular orbit memory 42c. Analogously, output data generated during the linear or line orbit $g_{line}(\beta,\Phi)$ is stored in a line orbit memory 42l. Zero padding means 44c and 44l add zeros around the collected two-dimensional data $g(\beta,\Phi)$ to enlarge the data to the next largest array which is an even power of 2 (e.g. 128×128; 256×256; 512×512; etc.). In the preferred embodiment, the circular and line orbit memories have this larger capacity and the zero padding means merely fills the unused memory cells with zeros. By surrounding the data with zeros in this manner, aliasing in the constructed image is reduced.

Figure 2:
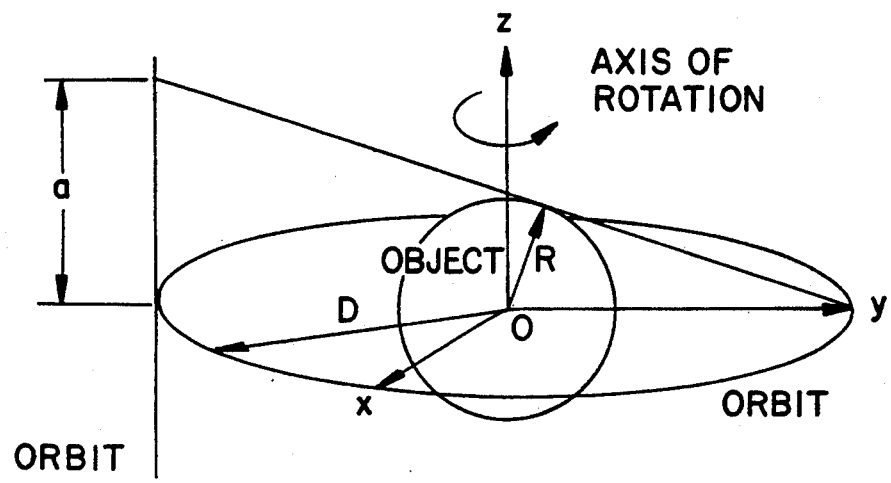
FIG. 2 illustrates the circular and linear orbits between the subject and detector in accordance with the present invention.

With continuing reference to FIG. 1A and further reference to FIG. 2, the full ray transform of the circle data is multiplied by a two-dimensional filter kernel $F_{circle}(\omega)$ in the frequency domain which is defined as:

$$F_{circle}(\omega_x,\omega_y)=1 \text{ for } D|\omega_y| \geq 0.5a|\omega_x|$$

$$F_{circle}(\omega_x,\omega_y)=0 \text{ for } D|\omega_y| \leq 0.5a|\omega_x| \quad (1),$$

where D is a radius of the circular orbit $\Phi$ of the circular cone-beam focal point and a, one half the length of the line orbit, is defined as:

$$a=2DR(D^2-R^2)^{-\frac{1}{2}} \quad (2),$$

where R is the radius of the subject or examination region. See FIG. 2.

Figure 1B:
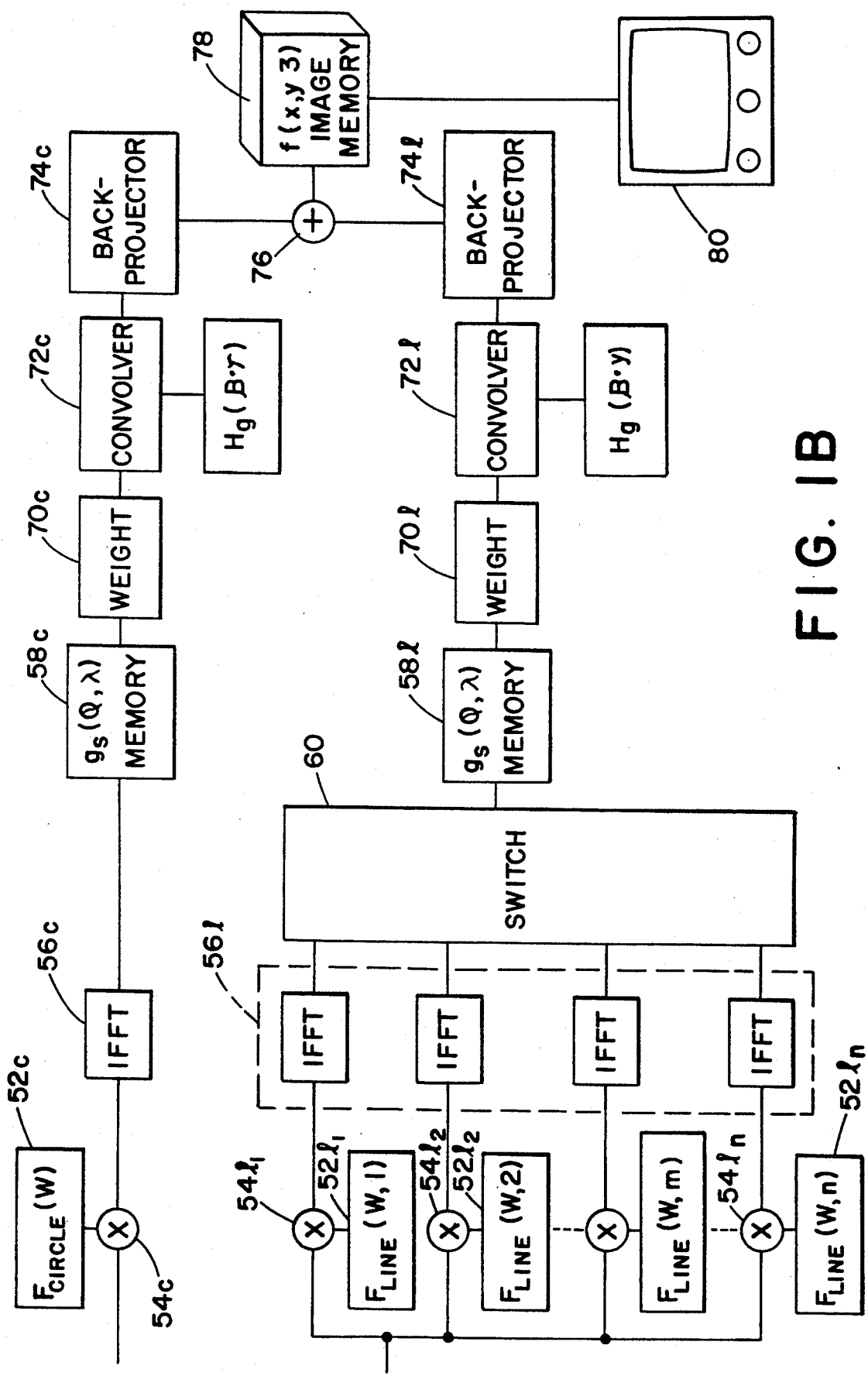

With continuing reference to FIG. 1A and further reference to FIG. 1B, a Fourier transform means 50c transforms the data $g_{circle}$ into the frequency domain. Preferably, the transform means 50c performs a two-dimensional fast Fourier transform. A filter means 52c monitors the circular orbit memory data $g_{circle}$ to determine whether $D|\omega_y|$ is greater than half $a|\omega_x|$. Frequency components are kept if the ratio of the frequency component in x (x is parallel to the plane of the circular orbit) over the frequency component in y (y is parallel to the axis of rotation) is greater than or equal to the ratio of two times the focal length over one half the length of the linear translation. Frequency components that do not satisfy this condition are discarded. A multiplying means 54c multiplies each Fourier transformed value by one or zero, i.e. keeps or discards it, in accordance with the filter function $F_{circle}$ and Equation (1). A frequency domain to spatial domain transform means 56c transforms the filtered circular orbit data back to the spatial domain. The resultant filtered spatial domain data $g_s(\phi,\lambda)$ is stored in a filtered spatial domain data memory 58c. In this manner, the circular orbit data is transformed into the frequency domain, filtered or edited to remove redundant data with the line orbit data, and returned to the spatial domain.

The line orbit data $g_{line}$ is also transformed into the frequency domain and filtered. However, the filter for the line orbit data is spatially varying. That is, a different filter kernel is needed for each row of data, where a row is parallel to the circular orbit plane.

More specifically to the preferred embodiment, a spatial to frequency domain transform means 50$l$, such as a fast Fourier transform means, transforms the zero padded line data $g_{line}$ into the frequency domain. In the frequency domain, data is operated upon with a series of line orbit filters $F_{line}(\omega,1)$, $F_{line}(\omega,2)$, ..., $F_{line}(\omega,n)$ to remove the redundant data with the circular orbit. The line filter function is defined as:

$$F_{line}(\omega_x,\omega_y,row) = 1 \text{ for } b(row)|\omega_y| \geq D|\omega_x| \text{ and } row < 0.5a$$

$$F_{line}(\omega_x,\omega_y,row) = 0 \text{ for } b(row)|\omega_y| < D|\omega_x| \text{ or } row > 0.5a \quad (3),$$

where the distance between each row is equal to the distance between the centers of the sampled bins in the projections and b(row) is defined as:

$$b(row) = ((0.5a)^2 - (row)^2)^{\frac{1}{2}} \quad (4)$$

Thus, for each row, the Fourier transform of the data is compared with different boundary conditions to determine whether it is kept or rejected. A series of line data filter means 52$l_1$, 52$l_2$, ..., 52$l_n$ determine whether the boundary conditions of Equation (3) are met for each row. More specifically, the line orbit filter means determines whether the boundary conditions are met for a first row and causes a multiplying means 54$l_1$ to multiply each Fourier transformed data value by the zero or one of line filter function, $F_{line}(\omega,1)$ i.e. accepts or rejects it. Similarly, the Fourier transform of the line data is multiplied by means 54$l_2$ by the second line filter function $F_{line}(\omega,2)$. This process is repeated for each of n line filter functions. The value n is the smallest integer greater than 0.5 a, where a is measured in bin width units. In the geometry of the preferred embodiment, n=26. In this manner, the redundant data is removed.

A frequency domain to spatial domain transform means 56$l$ transforms the two-dimensional data from the frequency domain back to the spatial domain to generate filtered data values $g_s(\phi,\lambda)$. A switching means 60 switches filtered line orbit data into rows of a filtered line orbit data means 58$l$. More specifically, row 1 of the data filtered by filter $F_{line}(\omega,1)$ is loaded into row 1 of the memory 58$l$ and row −1 of the data filtered by filter $F_{line}(\omega,1)$ is loaded into row −1 of the memory 58$l$. Similarly, the ±mth row of the data filtered by filter $F_{line}(\omega,m)$ is loaded into the ±mth row of the memory 58$l$. Rows of memory 58$l$ beyond the ±nth rows are loaded with zeros.

Figure 4:
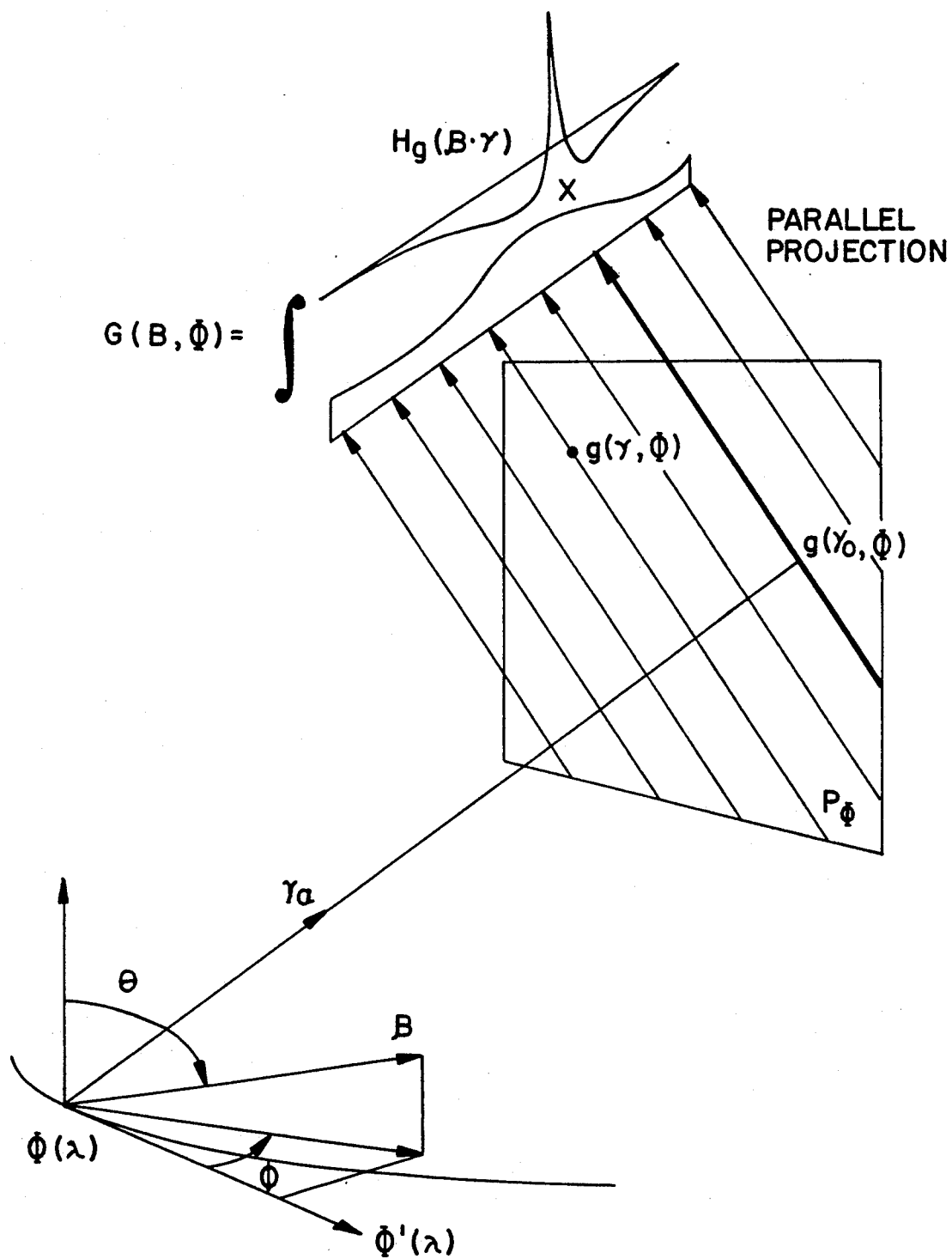
FIG. 4 is illustrative of the generation of the intermediate function $G(\beta,\Phi)$.

The line orbit and circular orbit data are reconstructed into the image representation by weighting and convolution backprojection. Preweighting means 70$c$ and 70$l$ preweight the data values in memories 58$c$ and 58$l$. Convolution means 72$c$ and 72$l$ convolve each row of weighted data with a convolution function $H_g(\beta\cdot\gamma)$. The filter kernel $H_g(\beta\cdot\gamma)$ illustrated in FIG. 4 is preferably a convolution function defined as:

$$H_g(\beta,\gamma) = \frac{1}{\epsilon} \quad \text{for } |\beta \cdot \gamma| < \epsilon \quad (5)$$

$$H_g(\beta,\gamma) = \frac{-1}{(\beta \cdot \gamma)^2} \quad \text{for } |\beta \cdot \gamma| \geq \epsilon.$$

That is, the data in each pixel is subtractively combined with a fraction of the data from adjoining pixels in the same row. The fraction of the closest adjoining pixels is highest tapering off as the pixels become further away. Backprojectors 74$c$ and 74$l$ backproject the circular orbit convolved data and the line orbit convolved data, respectively. A summing means 76 adds the backprojected circle and line orbit data into an image memory 78. A resultant image f(x,y,z) for the circular volume of radius R is created in the image memory 78. Selected portions, planes, and projections of the image data in the image memory 78 are selectively displayed on a video monitor 80 or other conventional display medium.

Figure 3:
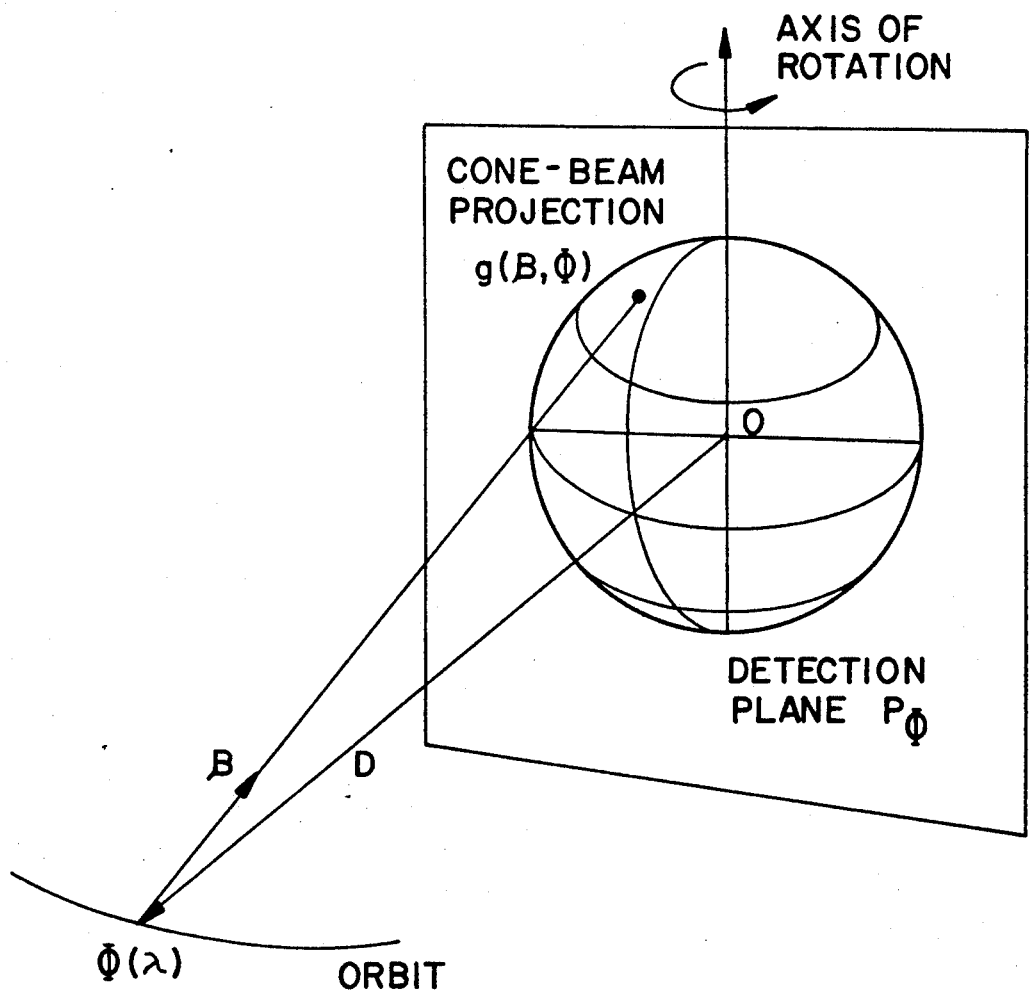
FIG. 3 is illustrative of cone-beam geometry.

The cone-beam geometry is shown in FIG. 3. The focal point trajectory is referred to as "orbit". The focal length D is the distance between the focal point and the axis of rotation. The detection plane P is assumed to be at the axis of rotation. This assumption is always valid if one scales up the object by moving the axis of rotation on the detection plane when reconstructing the image. The object density function is f(x), where x is a vector in $R^3$. The cone-beam data may be expressed as:

$$g(\beta\Phi) = \int_{-\infty}^{\infty} f(\Phi + t\beta)dt, \quad (6)$$

where $\Phi$ is the orbit vector for the location of the focal point, and $\beta$ is a unit-vector of the ray direction. The goal is to reconstruct the object f(x) from the cone-beam projections $g(\beta,\Phi)$.

Smith, supra, defined a one-dimensional filter kernel as:

$$H_g(t) = \frac{1}{\epsilon^2} \quad (|t| < \epsilon)$$

$$H_g(t) = \frac{-1}{t^2} \quad (|t| \geq \epsilon). \quad (7)$$

This is the famous ramp filter widely used in tomography. An intermediate function $G(\beta,\Phi)$ is obtained from the two-dimensional cone-beam projection data g:

$$G(\beta,\Phi) = 2 \lim_{\epsilon \to 0} \int_S H(\beta \cdot \gamma)g(\gamma,\Phi)d\gamma, \quad (8)$$

where S denotes (any) half of the unit sphere, and $d\gamma$ is the surface element on the unit sphere.

Figure 5:
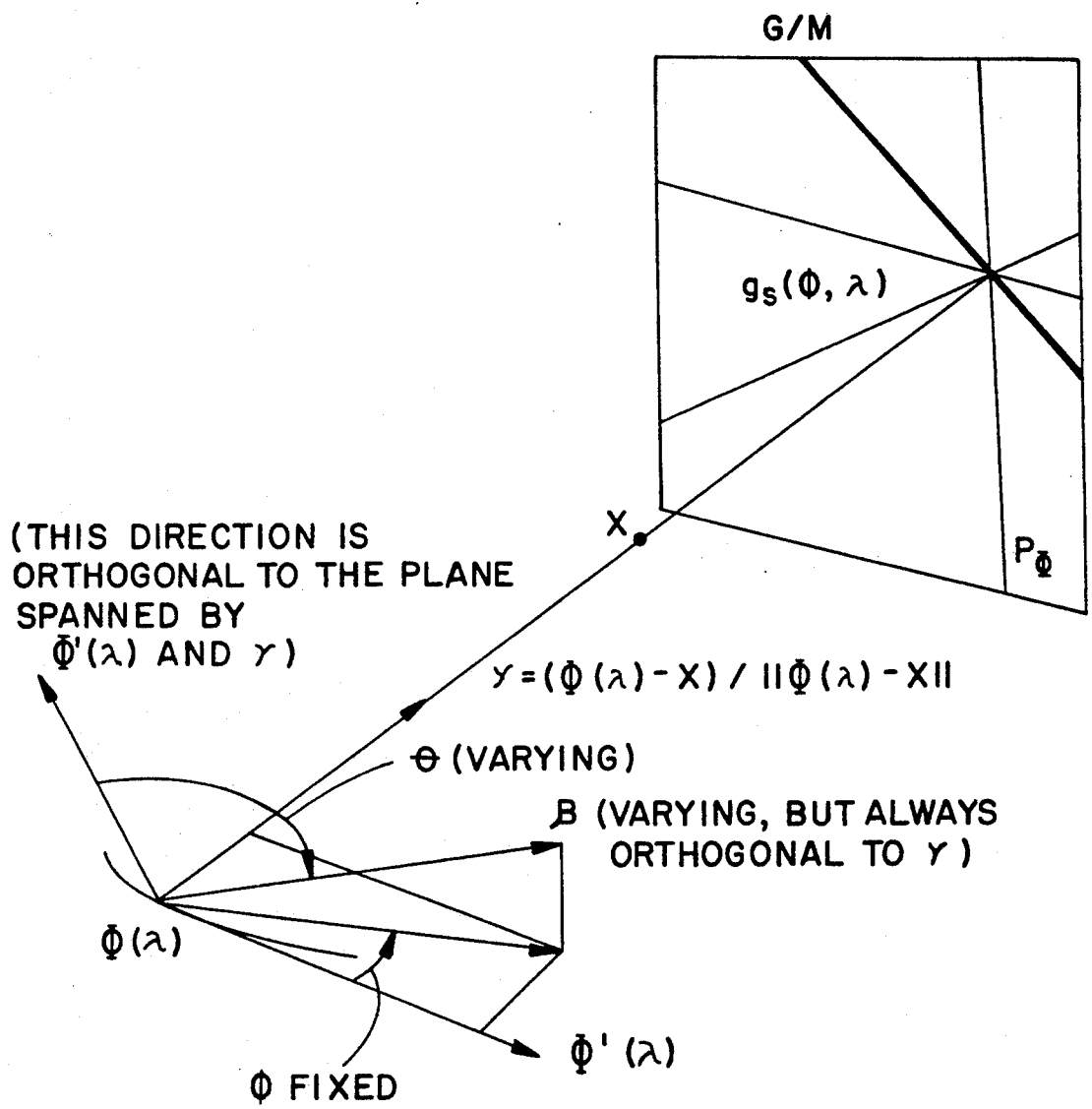
FIG. 5 illustrates the local coordinate system for the projection data.

Modified projection data $g_s$ is obtained from G by:

$$g_s(\phi,\lambda) = \int_0^\pi \frac{G(\beta_L(\theta,\phi),\Phi(\lambda))}{M(\beta_L(\theta,\phi),\Phi(\lambda))} d\theta, \quad (9)$$

where $\theta$ and $\phi$ are the azimuth and longitude of vector $\beta_L$, respectively in the local coordinate system as shown in FIG. 5, and $\lambda\epsilon\Lambda$ is the real parameter of orbit $\Phi$. In Equation (9), the function $M(\beta_L,\Phi)$ denotes the number of times the orbit intersects the plane which is represented by the normal vector $\beta_L$ and passes through point $\Phi(\lambda)$. Finally, the inversion formula is:

$$f(x) = \frac{1}{8\pi^4} \int_\Lambda \frac{1}{\|x - \Phi\|^2} \lim_{\epsilon \to 0} \int_0^\pi g_s(\phi,\lambda) H_g(\cos(\phi' - \phi)) |\cos\phi| d\phi \|\Phi'(\lambda)\| d\lambda \quad (10)$$

It is observed that Equation (10) is the same as Feldkamp's algorithm if the orbit is a circle ($\|\Phi'(\lambda)\| = D$) and $g_s$ is cone-beam projection data.

If $g_s$ is easily obtained, the image $f(x)$ can be reconstructed by Equation (10). The difficulty lies in evaluating Equation (9), where the function $M(\beta_L,\Phi)$ is very complicated. For the one-circle and a perpendicular-line orbit geometry, $M(\beta_L,\Phi)$ can take values of 1, 2, 3, and infinity. There hardly exists an analytical expression for $M(\beta_L,\Phi)$.

In order to simplify the evaluation of $g_s$, one should study Equations (8) and (9) first FIG. 4 illustrates an intuition of Equation (8). At a fixed focal point location $\Phi$ which is associated with a detection plane $P_\Phi$, consider a direction $\beta$. The unit vector $\beta$ has an azimuth $\theta$ and a longitude $\phi$, where $\phi$ is in the orbit plane which is spanned by $\Phi(\lambda)$ and $\Phi'(\lambda)$. The inner product $\beta \cdot \gamma$ = constant corresponds to a straight line on the detection plane $P_\Phi$. In FIG. 4, $\beta \cdot \gamma_0 = 0$. The intermediate function $G(\beta,\Phi)$ can be formed in three steps. (1) Treat the detection plane $P_\Phi$ as a two-dimensional image plane, and perform parallel projection along the direction of $\beta \cdot \gamma$ = constant. (2) Weight the one-dimensional projected data by $H_g(\beta \cdot \gamma)$. (3) Integrate these weighted one-dimensional data to obtain the value of $G(\beta,\Phi)$. Thus, one may refer to Equation (8) as "projection" and "filtering".

FIG. 5 depicts the procedure in Equation (9). If one again treats the detection plane $P_\Phi$ as a two-dimensional image plane, this is a "weighted backprojection". In FIG. 5, a local coordinate system is used, where the longitude $\phi$ of vector $\beta_L$ is fixed, and the azimuth $\theta$ is varying. The vector $\gamma$ is orthogonal to all these varying $\beta_L$'s. If $M(\beta_L,\Phi) = 1$, $g_s$ is the backprojection of $G(\beta_L,\Phi)$, and $g_s(\phi,\lambda) = g(\gamma,\Phi)$ because this whole procedure is the standard filter backprojection algorithm. Usually, $M(\beta_L,\Phi)$ is not constant, the backprojection is weighted by $1/M(\beta_L,\Phi)$, and thus $g_s(\phi,\lambda) \neq g(\gamma,\Phi)$.

Referring to FIG. 2, the orbits consist of a circle (in the x-y plane) and a perpendicular line (parallel to the z-axis). Suppose that the object is defined in the sphere $\|X\| < R$ as shown in FIG. 2, then the required half-length a of the line-orbit is $2DR(D^2 - R^2)^{-\frac{1}{2}}$. Any plane cutting through the object will intersect the orbit, and may intersect the orbit 1, 2, 3, or infinity times.

Figure 6A:
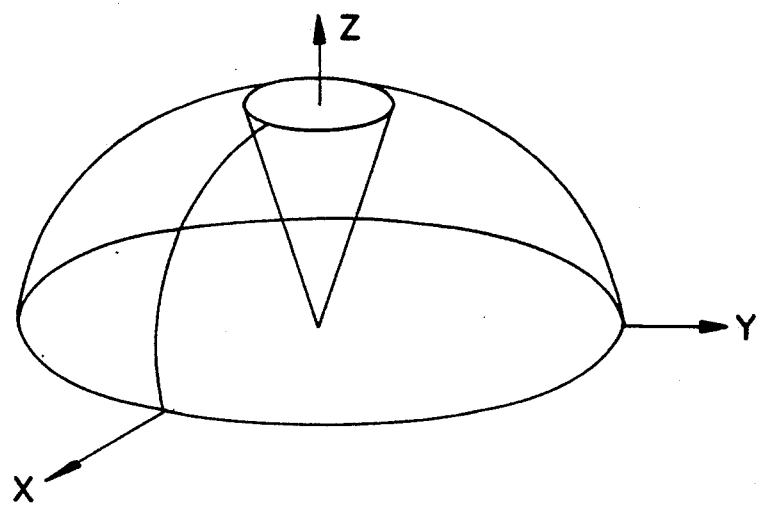
FIGS. 6A and 6B illustrate regions of the plane normal to group I and group II.
Figure 6B:
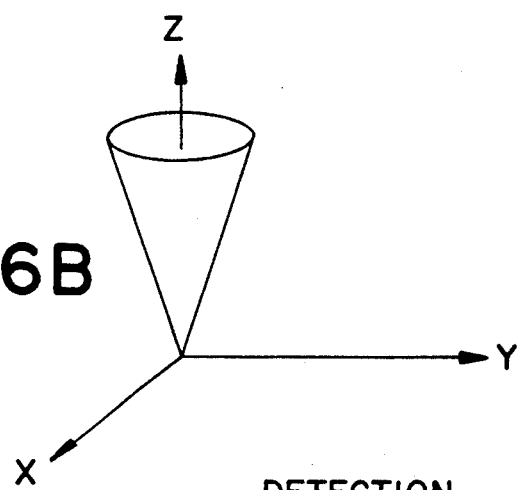

The plane that cuts through the object is referred to as to a "cutting plane", and the "plane angle" is defined as the angle made of the plane normal to the z-axis. A cutting plane with a plane angle less than $\sin^{-1}(R/D)$ intersects the linear orbit; and a cutting plane with a plane angle greater than $\sin^{-1}(R/D)$ intersects the circular orbit. Some cutting planes may intersect both orbits. The cutting planes can be divided into two groups: (1) with plane angle $> \sin^{-1}(R/D)$, and (2) with plane angle $< \sin^{-1}(R/D)$ as shown in FIG. 6. The circular orbit is used to reconstruct the data from group one, and use the linear orbit to reconstruct the data from group two. The circular orbit offers all the data in group one, and some data not in group one. The data not in group one are discarded by reducing the integral interval in Equation (9). For the circular orbit, therefore, one can use $M(\beta_L,\Phi) = 2$ in Equation (9) with modified integral limits.

Employing the two-dimensional central-slice theorem, the modification procedure of Equations (8) and (9) is equivalent to filtering $g(\beta,\Phi)$ by $F_{circle}(\omega)$, which is a two-dimensional filter kernel in the frequency domain and is defined by:

$$F_{circle}(\omega) = 1 (D|\omega_y| \geq 0.5a|\omega_x|)$$

$$F_{circle}(\omega) = 0 (D|\omega_y| < 0.5a|\omega_x|) \quad (11),$$

with $\omega = (\omega_x, \omega_y)$. Filter $F_{circle}(\omega)$ is applied to the cone-beam projections from the circular orbit. For each projection angle, $g_s$ is obtained by:

$$g_s = IFFT(F_{circle}(\omega) \times FFT(g)) \quad (12),$$

where FFT is the two-dimensional fast Fourier transform operator and IFF is the two-dimensional inverse fast Fourier transform operator. In order to avoid aliasing, g is zero-padded before taking the FFT.

Figure 7:
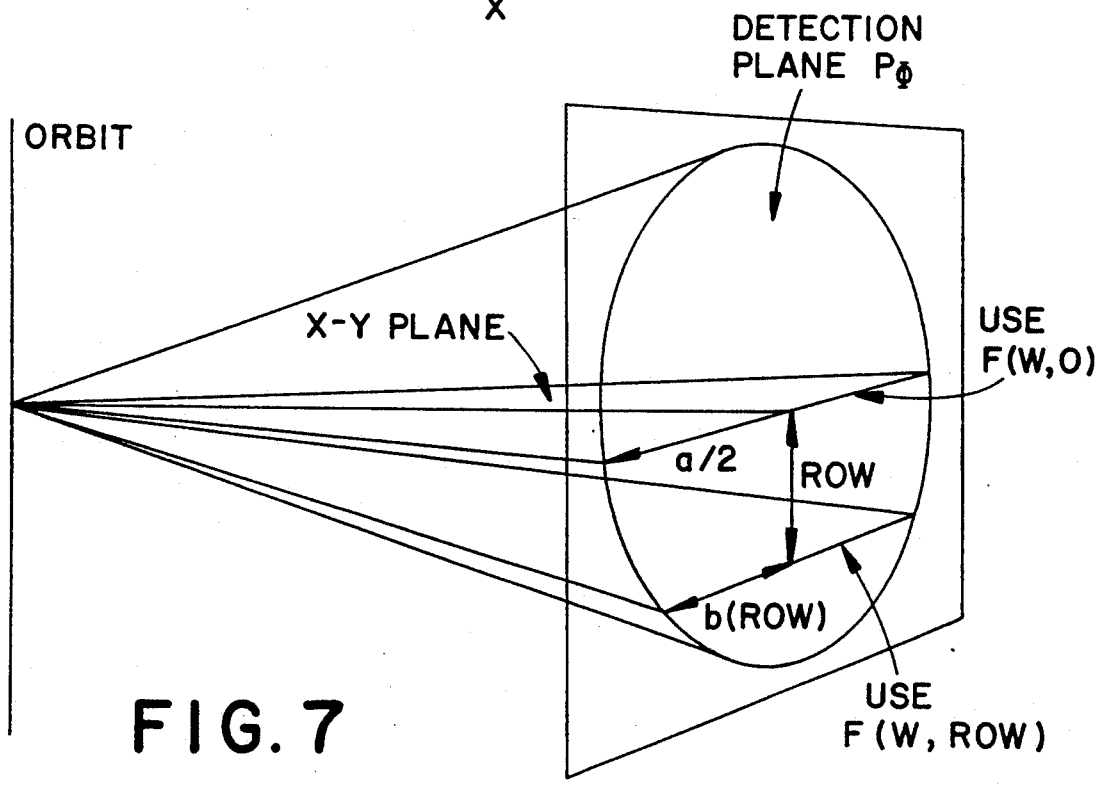
FIG. 7 illustrates the linear orbit relationships in which the filter is spatially varying with different filters for different rows.

The linear orbit offers all the data in group two, and some data not in group two. The data not in group two are discarded by reducing the integral interval in Equation (9). For the linear orbit therefore, one can use $M(\beta_L, \Phi) = 1$ in Equation (9) with modified integral limits. However, due to the cone-shape in FIG. 6, there exists no filter in the frequency domain, similar to $F_{circle}(\omega)$, that can be used to discard the unwanted data. A spatially varying two-dimensional filter is required, one filter kernel for each row. If each spatial domain filter kernel is transformed into the frequency domain one has:

$$F_{line}(\omega,row) = 1 (b(row)|\omega_y| \geq D|\omega_x|) \text{ and } (row < 0.5a)$$

$$F_{line}(\omega,row) = 0 (b(row)|\omega_y| < D|\omega_x|) \text{ or } (row > 0.5a) \quad (13),$$

where row is the distance between the cone-beam projection data point and the x-y plane, and b(row) is defined as:

$$b(row) = \sqrt{0.25a^2 - row^2} \quad (14),$$

and is illustrated in FIG. 7. Thus, a certain row in $g_s$ is obtained by:

$$g_s = IFFT(F_{line}(\omega,row) \times FFT(g)) \quad (15),$$

A different filter is used for a different row in $g_s$.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. An apparatus for generating an image representation of an interior portion of a subject, the apparatus comprising:

a radiation detection means for receiving radiation travelling along a cone of rays which converge at a focal point and generating electrical data indicative thereof;

a means for moving the radiation detecting means in a circular orbit such that the radiation detection means generates circular orbit data and in a line orbit such that the radiation detection means generates line orbit data;

a Fourier transforming means for transforming the circular orbit and line orbit data into a frequency domain;

a circular orbit filtering means for filtering the frequency domain circular orbit data to discard a portion which is redundant with the line orbit data;

a line orbit filtering means for repeatedly filtering the line orbit data with a series of spatially variant line orbit data filter functions, each line orbit data filter function corresponding to one of a plurality of slices of line orbit data;

an inverse Fourier transforming means for transforming a filtered circular orbit data and the filtered line orbit data from the frequency domain to a spatial domain;

a backprojection means for reconstructing the spatial domain filtered circular orbit data and line orbit data into a three-dimensional image representation;

an image memory means for storing the three-dimensional image representation.

2. The apparatus as set forth in claim 1 further including a monitor means for converting a portion of the image representation into a man-readable display.

3. The apparatus as set forth in claim 1 further including a zero padding means for adding zeros peripherally around the circular and line orbit data generated by the radiation receiving means.

4. The apparatus as set forth in claim 1 further including:
a filtered line orbit data memory means;
a switching means for loading ±mth rows of the inverse Fourier transformed data that was filtered with an mth of the line orbit data filter functions into ±mth rows of the filtered orbit data memory means, the backprojecting means reconstructing spatial domain filtered line orbit data from the filtered line orbit data memory means.

5. The apparatus as set forth in claim 1 wherein the subject is a patient which is injected with a radiopharmaceutical and wherein the radiation detecting means includes a cone-beam collimator mounted to a radiation receiving face of a gamma camera head.

6. The apparatus as set forth in claim 5 further including a video monitor for converting at least portions of the image representation in the image memory into a man-readable display.

7. A method of generating a diagnostic image representation of an interior portion of a subject, the method comprising:
receiving radiation along a cone of rays which converge at a focal point while:
causing relative movement between the subject and the focal point such that the focal point defines a circular orbit to collect circular orbit data,
causing relative movement between the subject and the focal point such that the focal point defines a line orbit orthogonal to a plane of the circular orbit to collect line orbit data;

transforming the circular orbit data into a frequency domain, discarding a selected portion of the frequency domain circular orbit data, and transforming the remaining frequency domain circular orbit data from the frequency domain to a spatial domain;

transforming the line orbit data into the frequency domain, in the frequency domain:
(a) operating on the frequency domain data with a first filter function to eliminate duplicative data relative to a first row,
(b) repeating step (a) for a plurality of rows with corresponding filter functions,
(c) transforming the rows of data from the frequency domain to the spatial domain;

performing a filtered backprojection on the spatial domain circular orbit data and the line orbit data to generate a three-dimensional image representation.

8. The method as set forth in claim 7 further including converting a portion of the image representation into a man-readable display.

9. The method as set forth in claim 7 further including expanding the size of the circular and line orbit data by adding zeros peripherally therearound for reducing reconstruction artifacts.

10. The method as set forth in claim 7 wherein the step of discarding the selected portion of the frequency domain circular orbit data includes operating on the frequency domain circular orbit data with a filter function which assumes a value of when a ratio of a frequency component in a direction parallel to a plane of the circular orbit over a frequency component in a direction parallel to an axis of rotation is greater than or equal to a ratio of twice a focal length over one half a length of the line orbit and assumes a zero value otherwise.

11. The method as set forth in claim 7 wherein the reconstructed image representation represents a spherical examination region and wherein the frequency domain line orbit data filter function has a value of 1 when both (1) a ratio of a frequency component in a direction parallel to an axis of rotation over a frequency component parallel to a plane of the circular orbit is greater than or equal to a ratio of a focal length over one half a length of a cord, along the corresponding row, with radius equal to one fourth a length of the line orbit and centered at a center of a radiation detector and (2) a distance between the corresponding row and a centermost row is smaller than one fourth the length of line orbit and has a value of zero otherwise.

12. The method as set forth in claim 7 wherein the step of generating circular and line orbit data includes:
injecting a subject with a radiopharmaceutical;
collimating radiation from the radiopharmaceutical through a cone-beam collimator;
detecting radiation that has traversed the cone-beam collimator with a gamma camera head;
moving the gamma camera head in a circular orbit to collect the circular orbit data;
moving the gamma camera head in a straight line transverse to the circular orbit to collect the line orbit data.

13. A method of reconstructing an image representation of an interior portion of a subject, the method comprising:
moving a focal point of a cone-beam radiation detection system along (1) a circular orbit and (2) a line orbit and collecting circular orbit and line orbit data;

transforming the circular orbit data into a frequency domain and filtering the circular orbit data in the frequency domain to remove data which is redundant with the line orbit data;

transforming the line orbit data into the frequency domain and filtering the line orbit data with a series of different filter functions to define a plurality of slices each with redundant circular orbit data removed;

reconstructing the filtered circular and line orbit data into a three-dimensional image representation.

14. The method as set forth in claim 13 wherein the line orbit has a length equal to $2DR(D^2-R^2)^{-\frac{1}{2}}$, where R is a radius of the interior subject portion that is reconstructed into the image representation and D is a radius of the circular orbit.

* * * * *